United States Patent
Elgas

[19]

[11] Patent Number: 6,045,752
[45] Date of Patent: Apr. 4, 2000

[54] BLOOD OXYGENATOR WITH WATERLESS HEAT EXCHANGER

[75] Inventor: Roger J. Elgas, Anaheim Hills, Calif.

[73] Assignee: Medtronic, Inc., Minneapolis, Minn.

[21] Appl. No.: 08/618,473

[22] Filed: Mar. 18, 1996

[51] Int. Cl.[7] .................................................. A61M 1/14
[52] U.S. Cl. .............................. 422/46; 422/48; 604/4; 261/DIG. 28; 62/3.3; 62/3.7
[58] Field of Search ........................... 422/46, 48; 604/4; 261/DIG. 28; 62/3.3, 3.7, 58

[56] References Cited

U.S. PATENT DOCUMENTS

| | | |
|---|---|---|
| 3,399,536 | 9/1968 | Walz . |
| 3,971,435 | 7/1976 | Peck ........................................... 165/78 |
| 4,213,703 | 7/1980 | Haunold et al. ......................... 356/244 |
| 4,407,133 | 10/1983 | Edmonson .................................. 62/3.3 |
| 4,476,685 | 10/1984 | Aid ............................................. 62/3.3 |
| 4,574,876 | 3/1986 | Aid . |
| 4,585,056 | 4/1986 | Oscarsson ................................ 165/133 |
| 4,707,587 | 11/1987 | Greenblatt ............................... 219/299 |
| 5,266,265 | 11/1993 | Raible ........................................ 422/46 |
| 5,429,184 | 7/1995 | Bach et al. .............................. 165/149 |
| 5,470,531 | 11/1995 | Sjorgren et al. .......................... 422/46 |

FOREIGN PATENT DOCUMENTS

| | | |
|---|---|---|
| 0582959 | 2/1994 | European Pat. Off. . |
| 0621047 | 10/1994 | European Pat. Off. . |

Primary Examiner—Christopher Kim
Attorney, Agent, or Firm—Harry G. Weissenberger

[57] ABSTRACT

Waterless temperature control of blood in a blood oxygenator is achieved by providing a non-disposable heater/cooler with a temperature-controlled surface that can be intimately mated with a heat-conducting surface of a disposable blood heat exchanger associated with the oxygenator. Blood flows in a shallow path past the heat-conducting surface so that substantially all of the blood will assume the temperature of the heat-conducting surface as it flows past that surface.

6 Claims, 2 Drawing Sheets

BLOOD OXYGENATOR WITH WATERLESS HEAT EXCHANGER

FIELD OF THE INVENTION

This invention relates to blood oxygenators and more particularly to an oxygenator using a waterless heat exchanger separate and detachable from the oxygenation portion of the oxygenator.

BACKGROUND OF THE INVENTION

Blood oxygenators are well known and are routinely used to temporarily assume the function of the lungs in certain surgical procedures such as open heart surgery. Although the principal function of the oxygenator is to store blood and conduct an oxygen-carbon dioxide gas exchange with the patient's blood, it also traditionally serves the function of regulating the blood temperature as various phases of the surgery require.

In a conventional oxygenator, blood temperature is regulated by causing the blood to flow through a heat exchanger in which a heat exchange takes place through metal or plastic interfaces between the blood and a temperature-controlled stream of water. The heat exchanger is conventionally incorporated into the oxygenator so that the blood follows a continuous path in the oxygenator, first through the heat exchanger and then through the gas exchanger.

Whenever blood and water are present in the same device, there is an inherent danger that one may accidentally leak into the other and interfere with the patient's well-being. Also, the water connection lines to the oxygenator, which is usually mounted on the heart-lung machine, can become snagged and lead to accidents. Equipment is further required for controlling the water temperature.

Placing the temperature control equipment directly into the oxygenator would solve the water problem, but this is impractical because the required equipment would be too bulky to fit into a reasonably sized oxygenator, and because the equipment would be too expensive for incorporation in a disposable device, which the oxygenator must be.

SUMMARY OF THE INVENTION

The present invention solves the above-described problems of the prior art by providing, in an oxygenator, a heat exchanger in which a thin film of blood passes along an interface which intimately engages a corresponding interface on a permanent heater-cooler housing onto which the oxygenator is mounted for use. Various embodiments of the invention described herein deal with the geometry of the interfaces for uniform control of the blood temperature, i.e., a geometry such that no part of the blood path is more than about one or two millimeters from the interface. Examples of such a geometry are large, flat surfaces lying against each other; convoluted surfaces that plug into each other; or spiral vanes defining a uniformly thin blood path between them.

DETAILED DESCRIPTION OF THE PREFERRED EMBODIMENT

The detailed description set forth below in connection with the appended drawings is intended as a description of the presently preferred embodiments of the invention, and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
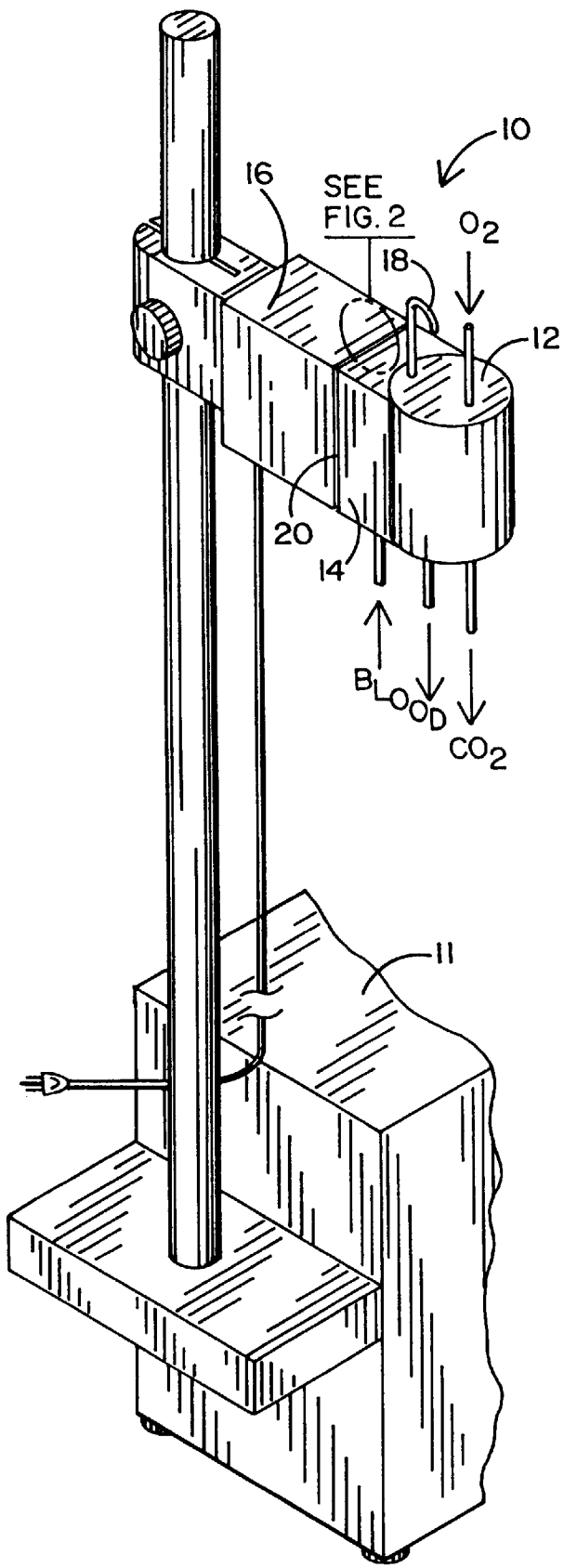
FIG. 1 is a schematic view showing the components of the inventive apparatus.

FIG. 1. shows the basic components of the apparatus 10 of this invention as mounted on a heart-lung machine 11: a blood oxygenator 12, a blood heat exchanger 14, and a heater/cooler 16. The heat exchanger 14 and the blood oxygenator 12 may be formed together in a single housing, or they may be separate and connected only operatively by tubing 18. The heater/cooler 16 may advantageously be a heat pump, or it may contain separate heating and cooling devices; in either event, it is preferably an electrical device of a conventional nature whose function is to maintain the interface 20 at a selectable temperature.

The interface 20 consists of two parts; the heat transfer face 22 which is part of the heater/cooler 16, and the heat transfer face 24 which is part of the blood heat exchanger 14. In all of the embodiments of the invention, it is important that the faces 22, 24 be in close physical contact with each other when the inventive apparatus is assembled. Preferably, the faces 22, 24 are made of metal, but either of them could also be made of other suitable materials that exhibit a high heat conductivity.

Because it is important that the blood flowing through the heat exchanger 14 be heated or cooled as uniformly as possible, it is desirable that no part of the blood path past the face 24 be more than a maximum distance d (preferably about 1–2 mm) away from the face 24. A corollary of this is that the area of the face 24 should be as large as possible, and that the blood flow past face 24 should be as slow as possible.

Figure 2:
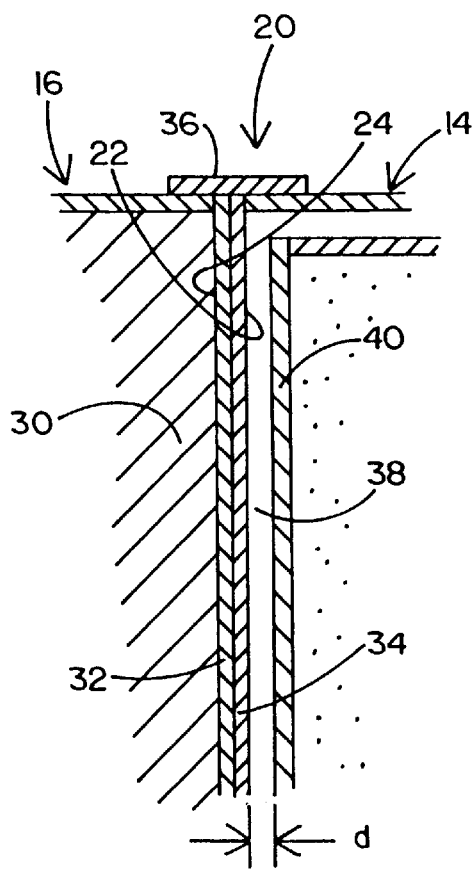
FIG. 2 is a detail sectional view illustrating one embodiment of the invention.
Figure 3:
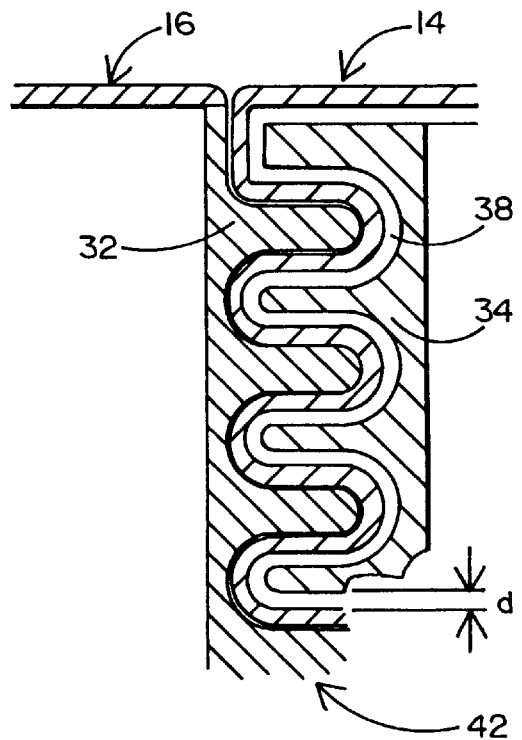
FIG. 3 is a detail sectional view illustrating another embodiment of the invention.
Figure 4:
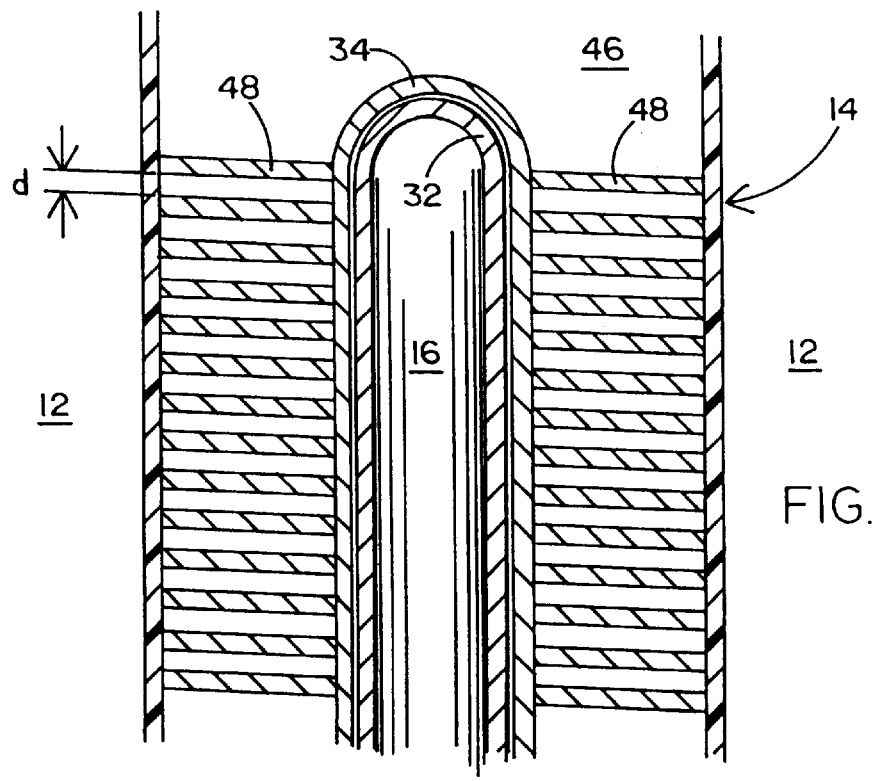
FIG. 4 is a detail sectional view illustrating a third embodiment of the invention.

The various embodiments shown in FIGS. 2-4 illustrate various ways in which this can be done. In FIG. 2, the heat pump or other heating/cooling device 30 of the heater/cooler 16 controls the temperature of a large, flat, preferably metallic plate 32 which constitutes face 22. The face 24 of the heat exchange 14 would in this case also be a flat plate 34 which lies in physical contact with the face 22 when the heat exchanger 14 is mounted on the heater/cooler 16 by an appropriate means such as a bracket 36. If the heat exchanger 14 is integrally formed with the oxygenator 12, the blood path 38 through the heat exchanger 14 would be the large, planar space, about 1–2 mm thick, between the plate 34 and the wall 40 of the oxygenator 12.

FIG. 3 illustrates a way of obtaining a larger interface area in a smaller area, by forming the plates 32 and 34 with intermeshing convolutions 42. The convolutions 42 may be so formed as to allow the heater/cooler 16 and the heat exchanger 14 to engage each other in the way an electric plug engages a wall outlet.

FIG. 4 shows an embodiment in which the heat exchanger 14 is arranged in the central core of the oxygenator 12. In that embodiment, the plate 32 takes the form of a generally cylindrical finger that extends into the oxygenator 12 and therein contacts the plate 34. In the embodiment of FIG. 4, the plate 34 is shaped to form a recess or socket 44 in the center of a generally cylindrical blood heat exchange chamber 46 extending through the central core of oxygenator 12.

In order to maintain a blood path in which no part of the path is more than the distance d from a heat exchange plate, the plate 34 is provided with metallic spiral fins 48 which extend from the plate 34 to the wall of the chamber 46. The fins 48 cause the blood to travel spirally around the plate 34 in a thin sheet while being continuously exposed to heat or cold which the fins 48 draw from the plate 34.

It is understood that the exemplary blood oxygenator with the waterless heat exchanger described herein and shown in the drawings represents only a presently preferred embodiment of the invention. Indeed, various modifications and additions may be made to such embodiments without departing from the spirit and scope of the invention. Thus, other modifications and additions may be obvious to those skilled in the art and may be implemented to adapt the present invention for use in a variety of different applications.

I claim:

1. A blood heat exchange system for a blood oxygenator, comprising;
   a) a non-disposable heater-cooler unit having a temperature-controlled external surface;
   b) a disposable oxygenator unit releasably matable with said heater/cooler unit, said oxygenator unit including:
      i) an oxygenation section arranged to oxygenate blood flowing therethrough; and
   c) said path being defined at least in part by a heat-conducting external surface of said oxygenator unit, said heat conducting surface being arranged to lie in intimate contact with said temperature-controlled surface when said heater/cooler unit and said oxygenator unit are mated;
   d) said path along said heat-conducting surface being sufficiently narrow so that the blood passing through said path will substantially uniformly assume the temperature of said heat-conducting surface as it passes said heat-conducting surface.

2. The blood heat exchange system of claim 1, in which said path is substantially 1–2 mm deep.

3. The blood heat exchange system of claim 1, in which said temperature-controlled surface and said heat-conductive surface are substantially flat plates.

4. The blood heat exchange system of claim 1, in which said temperature-controlled surface and said heat-conductive surface are mating convoluted plates.

5. The blood heat exchange system of claim 1, in which said temperature-controlled surface and said heat-conducting surface are disposed in a blood chamber in said oxygenator and are substantially concentric therewith, said heat-conducting surface having formed therein a shallow, heat-conducting spiral fin extending between said heat-conductive surface and the walls of said blood chamber to define a spiral path for said blood around said heat-conducting surface.

6. The blood heat exchange system of claim 1, in which said temperature-controlled surface and said heat-conducting surface are metallic.

* * * * *